(12) United States Patent
Ma

(10) Patent No.: US 10,604,627 B2
(45) Date of Patent: Mar. 31, 2020

(54) DIANHYDRIDES, POLYIMIDES DERIVED FROM BISCATECOL, METHODS OF MAKING, AND METHODS OF USE

(71) Applicant: King Abdullah University of Science and Technology, Thuwal (SA)

(72) Inventor: Xiaohua Ma, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 45 days.

(21) Appl. No.: 15/776,660

(22) PCT Filed: Nov. 10, 2016

(86) PCT No.: PCT/IB2016/056778
§ 371 (c)(1),
(2) Date: May 16, 2018

(87) PCT Pub. No.: WO2017/085601
PCT Pub. Date: May 26, 2017

(65) Prior Publication Data
US 2018/0371168 A1    Dec. 27, 2018

Related U.S. Application Data

(60) Provisional application No. 62/255,550, filed on Nov. 16, 2015.

(51) Int. Cl.
*C08G 73/10* (2006.01)
*C07D 307/94* (2006.01)

(52) U.S. Cl.
CPC ....... *C08G 73/1003* (2013.01); *C07D 307/94* (2013.01)

(58) Field of Classification Search
CPC ............ C08G 73/1007; C08G 73/1003; C07D 487/10; C07D 493/08
See application file for complete search history.

(56) References Cited

FOREIGN PATENT DOCUMENTS

| CN | 102617587 | * | 8/2012 |
| JP | 2006-213827 | * | 8/2006 |
| WO | 2015001422 |  | 1/2015 |

OTHER PUBLICATIONS

Swaidan et al Rational Design of Intrinsically Ultramicroporous Polyimides Containing Bridgehead-Substituted Triptycene for Highly Selective and Permeable Gas Separation Membranes, Macromolecules 2014, 47, 5104-5114, published on Jul. 15, 2014.*
Search Report and Written Opinion for PCT/IB2016/056778 dated Feb. 24, 2017.
Ma, et al., "Synthesis and Effect of Physial Aging on Gas Transport Properties of a Microporous Polyimide Delved from a Novel Spirobifluorene-Based Dianhyride", vol. 4, No. 2, Jan. 29, 2015, pp. 231-235.

* cited by examiner

*Primary Examiner* — Gregory Listvoyb
(74) *Attorney, Agent, or Firm* — Billion & Armitage; Lisbeth C. Robinson

(57) ABSTRACT

The present disclosure provides for a multi-anhydride, a polyimide, a method of making a dianhydride, a method making a multi-anhydride, a method of making a polyimide, and the like.

5 Claims, No Drawings

DIANHYDRIDES, POLYIMIDES DERIVED FROM BISCATECOL, METHODS OF MAKING, AND METHODS OF USE

CROSS-REFERENCE TO RELATED APPLICATIONS

This application claims the benefit of and priority to U.S. Provisional Application Ser. No. 62/255,550, having the title "DIANHYDRIDES, POLYIMIDES DERIVED FROM BISCATECOL, METHODS OF MAKING, AND METHODS OF USE," filed on Nov. 16, 2015, the disclosure of which is incorporated herein in by reference in its entirety.

BACKGROUND

Polyimides are among the most important high-performance glassy polymeric materials that exhibit exceptional thermal, chemical and mechanical properties. Consequently, they have been practically applied in a wide range of fields such as aerospace technology, electronics industry, and can be used for high temperature adhesion, membranes for separation, composite materials, and the like. Currently, the most important commercialized polyimides in practical usages are Kapton, Upilex, Matrimid, P84, and Ultem. However, these polyimides exhibit poor processability due to their high melting temperature and limited solubility in organic solvents, resulting in great restriction in practical usage. Microporous polyimides, formed by condensation of the dianhydrides and diamines containing site of contortion, have been developed to overcome these deficiencies. However, microporous polyimides are challenging to synthesize due, at least in part, to limitations of suitable monomers, especially those dianhydrides.

SUMMARY

Embodiments of the present disclosure provide for multi-anhydrides, polyimides, methods of making a dianhydride, methods making a multi-anhydride, methods of making a polyimide, and the like.

An embodiment of the present disclosure includes, among others, a method of making a dianhydride:

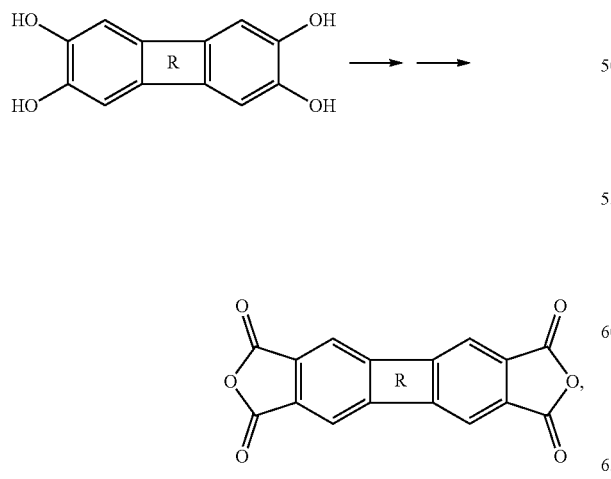

wherein R is selected from the following structures:

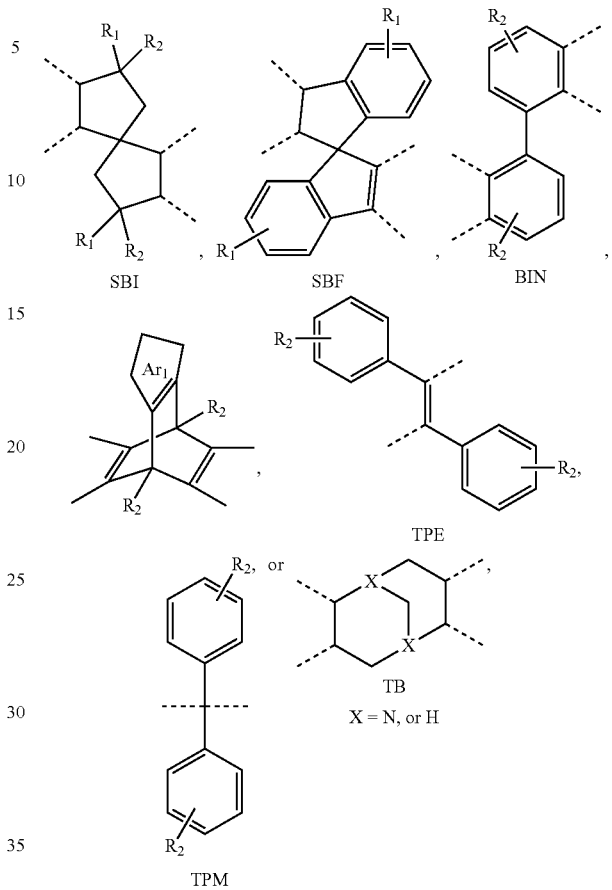

wherein each $R_1$ and $R_2$ are independently selected from the group consisting of: H, a linear or branched, substituted or unsubstituted, alkyl group, wherein when the bond is directed to the middle of a ring, this indicates that 1 to 4 of the R groups is optionally attached to the ring and each R group is independently selected from the other R groups attached to the ring, wherein $Ar_1$ is selected from the group consisting of: an aryl group and a heteroaryl group where each are substituted or unsubstituted.

In an embodiment, a method of making a multi-anhydride, among others, can include:

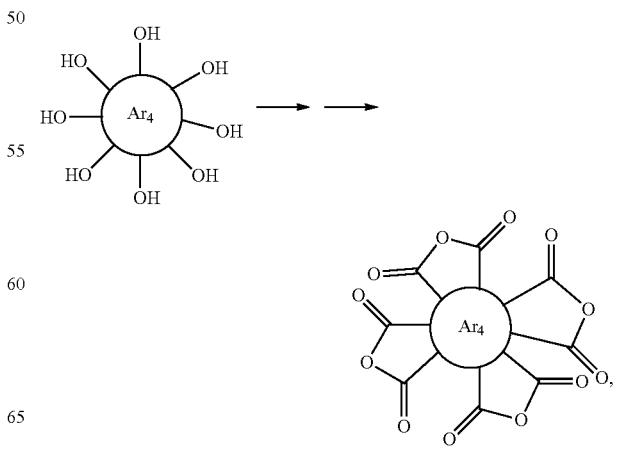

wherein Ar₄ is selected from the following structures:

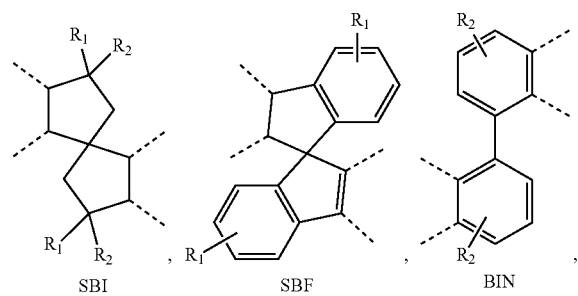

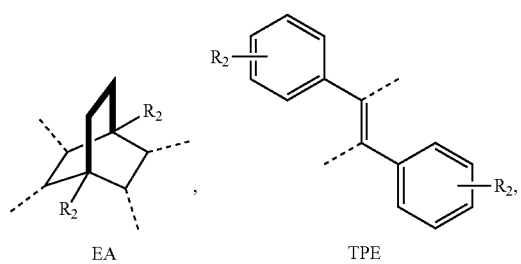

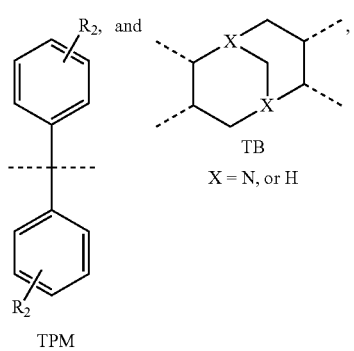

wherein each R₁ and R₂ are independently selected from the group consisting of: H, a linear or branched, substituted or unsubstituted, alkyl group, wherein when the bond is directed to the middle of a ring, this indicated that 1 to 4 of the R groups is optionally attached to the ring and each R group is independently selected from other R groups attached to the ring, wherein Ar₁ is selected from the group consisting of: an aryl group and a heteroaryl group where each are substituted or unsubstituted.

In an embodiment, a composition, among others, can include a polyimide having the following structure:

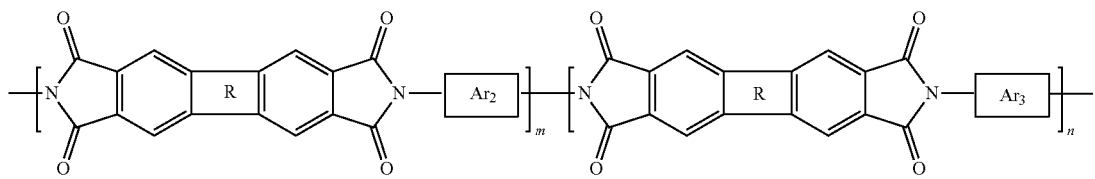

wherein Ar₂ and Ar₃ are aromatic diamines which are different from each other and wherein m and n can be 0 to 10,000.

In an embodiment, a composition, among others, can include a multi-anhydride comprising:

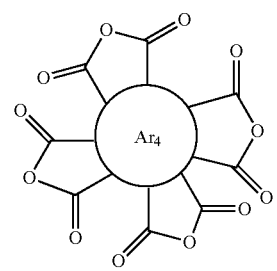

wherein Ar₄ is selected from the following structures:

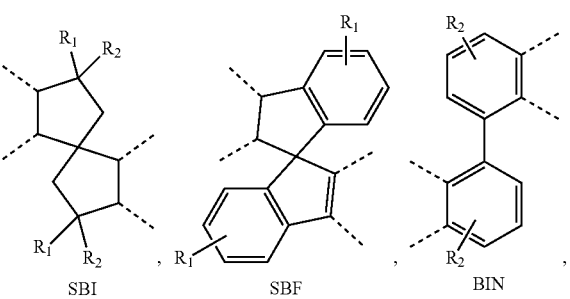

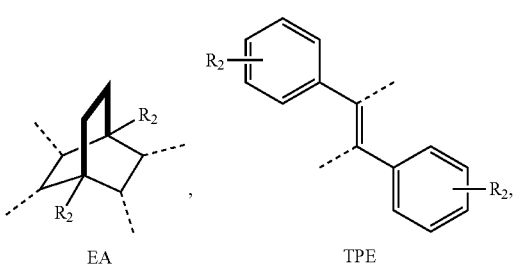

wherein Ar$_4$ is selected from the following structures:

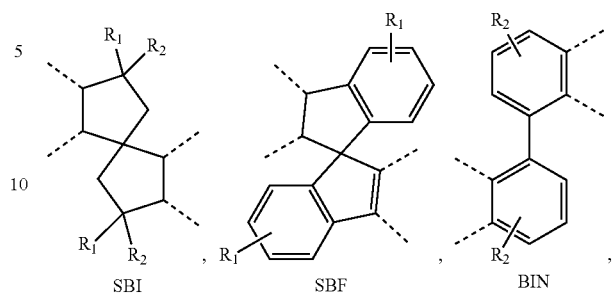

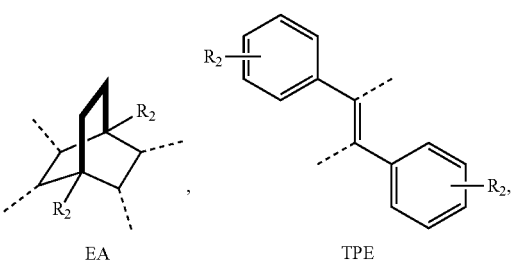

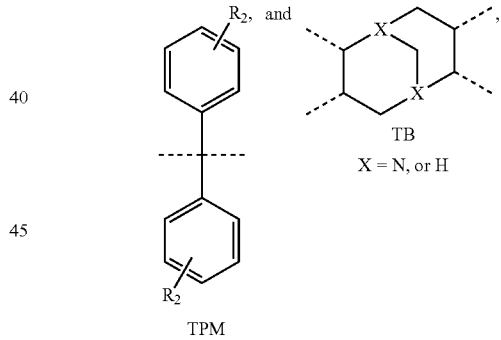

wherein each R$_1$ and R$_2$ are independently selected from the group consisting of: H, a linear or branched, substituted or unsubstituted, alkyl group, wherein when the bond is directed to the middle of a ring, this indicated that 1 to 4 of the R groups is optionally attached to the ring and each R group is independently selected from other R groups attached to a ring, wherein Ar$_1$ is selected from the group consisting of: an aryl group and a heteroaryl group where each are substituted or unsubstituted; wherein R$_6$ is H, a substituted or unsubstituted aromatic group or a linear or branched, substituted or unsubstituted, alkyl group; wherein R$_7$ and R$_8$ are each independently H, a substituted or unsubstituted aromatic group or a linear or branched, substituted or unsubstituted alkyl group, a hydroxyl group, a sulfonic group, and a thiol group.

In an embodiment, a composition, among others, can include a polyimide having the following structure:

wherein each R$_1$ and R$_2$ are independently selected from the group consisting of: H, a linear or branched, substituted or unsubstituted, alkyl group, wherein when the bond is directed to the middle of a ring, this indicated that 1 to 4 of the R groups is optionally attached to the ring and each R group is independently selected from other R groups attached to the ring, wherein Ar$_1$ is selected from the group consisting of: an aryl group and a heteroaryl group where each are substituted or unsubstituted.

In an embodiment, a method of making a polyimide, among others, can include:

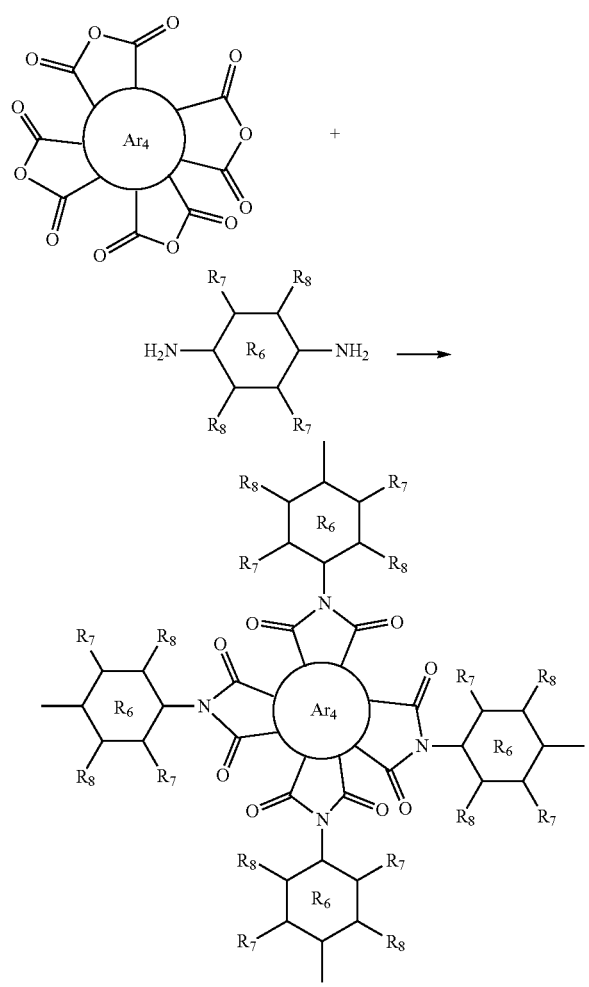

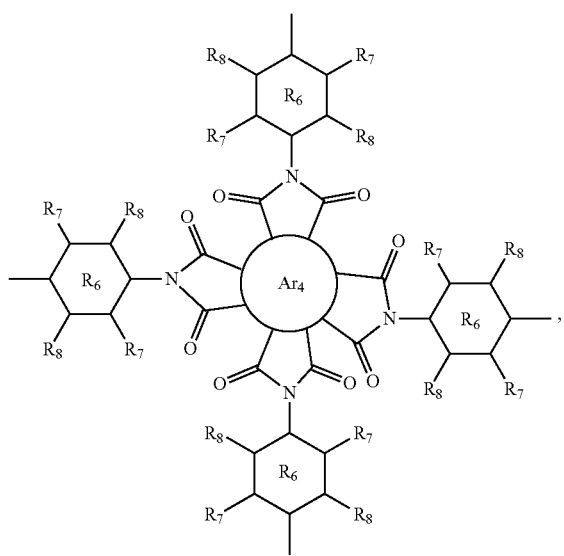

wherein Ar$_4$ is selected from the following structures:

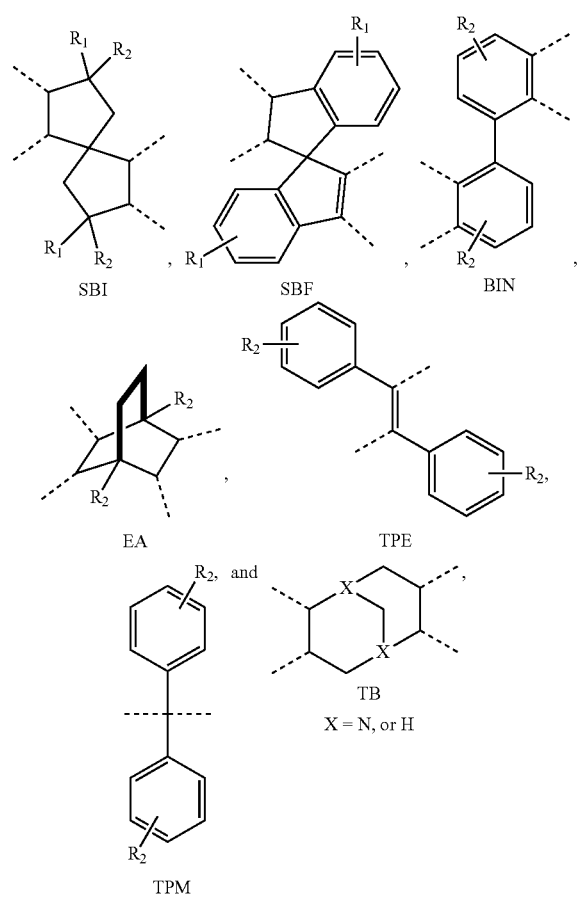

wherein each R$_1$ and R$_2$ are independently selected from the group consisting of: H, a linear or branched, substituted or unsubstituted, alkyl group, wherein when the bond is directed to the middle of a ring, this indicated that 1 to 4 of the R groups is optionally attached to the ring and each R group is independently selected from other R groups attached to a ring, wherein Ar$_1$ is selected from the group consisting of: an aryl group and a heteroaryl group where each are substituted or unsubstituted; wherein R$_6$ is H, a substituted or unsubstituted aromatic group or a linear or branched, substituted or unsubstituted, alkyl group; wherein R$_7$ and R$_8$ are each independently H, a substituted or unsubstituted aromatic group or a linear or branched, substituted or unsubstituted alkyl group, a hydroxyl group, a sulfonic group, and a thiol group.

Other compositions, methods, features, and advantages will be or will become apparent to one with skill in the art upon examination of the following drawings and detailed description. It is intended that all such additional compositions, methods, features and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, material science, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

Definitions

The term "substituted" refers to any one or more hydrogens on the designated atom that can be replaced with a selection from the indicated group, provided that the designated atom's normal valence is not exceeded.

As used herein, "aliphatic" or "aliphatic group" refers to a saturated or unsaturated, linear or branched, cyclic (non-aromatic) or heterocyclic (non-aromatic), hydrocarbon or hydrocarbon group and encompasses alkyl, alkenyl, and alkynyl groups, and alkanes, alkene, and alkynes, for example.

As used herein, "cyclic" group refers to a cyclic hydrocarbon having a stable 4, 5, 6, 7, 8, 9, 10, 11, or 12 membered (e.g., carbon or hetero), (unless the number of members is otherwise recited), monocyclic, bicyclic, or tricyclic cyclic ring.

As used herein, "alkyl" or "alkyl group" refers to a branched saturated aliphatic hydrocarbon. Examples of alkyl include, but are not limited to, methyl, ethyl, propyl, iso-propyl, sec-butyl, t-butyl, and iso-pentyl. A lower alkyl refers to an alkyl having 1 to 6 carbons.

The term "substituted," as in "substituted alkyl", "substituted aryl," "substituted heteroaryl" and the like means that the substituted group may contain in place of one or more hydrogens a group such as alkyl, hydroxy, amino, halo, trifluoromethyl, cyano, —NH(lower alkyl), —N(lower alkyl)$_2$, lower alkoxy, lower alkylthio, or carboxy, and thus embraces the terms haloalkyl, alkoxy, fluorobenzyl, and the sulfur and phosphorous containing substitutions referred to below, wherein "lower" refers to a group having 1 to 10 atoms.

As used herein, "halo", "halogen", or "halogen radical" refers to a fluorine, chlorine, bromine, and iodine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

The term "aryl" as used herein, refers to an aromatic monocyclic or multicyclic ring system of about 6 to about 14 carbon atoms, preferably of about 6 to about 10 carbon atoms. Exemplary aryl groups include phenyl or naphthyl, or phenyl substituted or naphthyl substituted.

The term "heteroaryl" is used herein to denote an aromatic ring or fused ring structure of carbon atoms with one or more non-carbon atoms, such as oxygen, nitrogen, and sulfur, in the ring or in one or more of the rings in fused ring structures. Preferred examples are furanyl, imidazyl, pyranyl, pyrrolyl, and pyridyl, The term "polyimide" as used herein is a group of polymers of imide monomers demonstrating heat- and chemical-resistant properties, and refers to either a homopolyimide or a copolyimide.

General Discussion

The present disclosure provides for dianhydrides, multi-anhydrides, polyimides, methods of making a dianhydride, methods making a multi-anhydride, methods of making a polyimide, and the like.

In the present disclosure, a unique synthetic route to prepare highly rigid, short dianhydride with site of contortion similar to PIMs is disclosed. Embodiments of the present disclosure include the synthetic method from bis-catecol to the corresponding dianhydride for intrinsic microporous polyimides (PIM-PIs). The original biscatecol for PIM-PIs can be the exact biscatecol for PIMs. These materials have potential for gas separation membranes, sensors, catalyst, and the like, For the synthesis of PIMs, the general step is as follows:

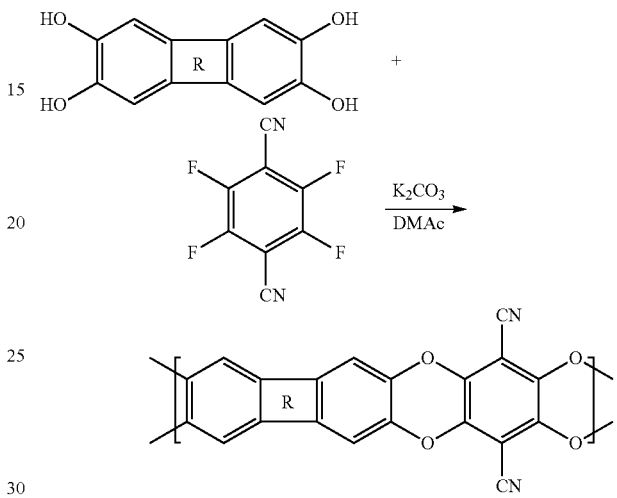

For the synthesis of PIM-PIs, the procedure is as follows:

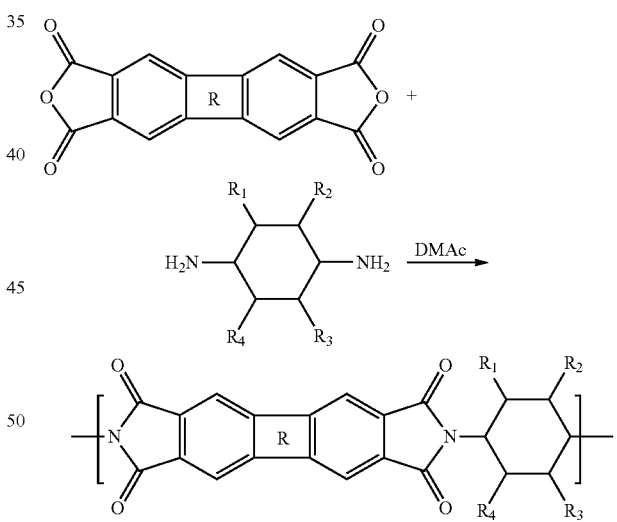

In the synthesis of PIM-PIs, an important intermediate is the dianhydride. In the present disclosure biscatecol is switched to dianhdyrides.

Embodiments of the present disclosure provide for preparing bulky aromatic dianhydrides from corresponding biscatechol and these can be advantageous for bridging the gap between the PIM and microporous polyimides, and also creates a novel platform for new linear porous polyimides and network polyimides. Advantageous applications of the highly microporous polyimides of the present disclosure include low birefringence polymers, membranes for gas and liquid separations, sensors and the like. Dianhydrides such as spirobisindane-, spirobifluorene- and ethanoanthracene-based non-extended dianhydrides have been synthesized according to the schemes described herein. Linear polyimides based on spirobisindane- and ethanoanthracene-based dianhydrides moiety have been synthesized and fully characterized.

Embodiments of the dianhydride-based polyimides have one or more of the following characteristics: intrinsic microporosity, good thermal stability, and enhanced solubility. Intrinsic microporosity is defined herein as a polymeric material with pore sizes of less than 2 nm and a surface porosity of >100 m$^2$/g, as determined by the nitrogen adsorption method at 77 K. Due to their good solubilities, thermal and chemical stabilities, and high microporosities, these materials can be implemented in a wide range of industrial applications related to aerospace industry, electronic industry, high temperature adhesion, membranes for separation, and composite materials.

Embodiments of the present disclosure include methods of making dianhydrides. In an embodiment the dianhydride formed is a highly rigid, short dianhydride such as an aromatic dianhydride from a biscatechol precursor, where the biscatechol precursor can have a variety of chemical configurations. In an embodiment, the method includes the following reaction scheme and the produced dianhydride:

The reaction conditions (e.g., reactants, solvents, temp, pH, concentration, and the like) for each step of the reaction scheme can be adjusted consistent with the teachings of this disclosure as long as the final product is formed. For example, in step one the NET$_3$ can be changed to another base, DCM can be switched to another solvent such as chloroform, tetrahydrofuran, dimethylformamide and dimethylacetamide, and the like, while the temperature can about room temperature to the boiling point of the solvent. In step 2 the catalyst can be another palladium catalyst such as PdCl$_2$, Pd$_2$(dba)$_3$, Pd(Ac)$_2$, and the like, while the ligand can be a ligand selected from PPh$_3$, dba, dppe, dppp, and the like. The solvent can be changed from DMF to DMAc, NMP, and the like, while the temperature of the reaction can be about 40 to 150° C. In step 3 ratio of EtOH and H$_2$O can be about 1:10 ratio to 10/1 ratio. In step 4 the reaction temperature can be about 100° C. to 140° C. and can reflux for about 1-48 hours. Additional details regarding the reaction scheme are described in the Examples.

In an embodiment, R can be one of the following structures (a dashed line can indicate how the group may be bonded to another group):

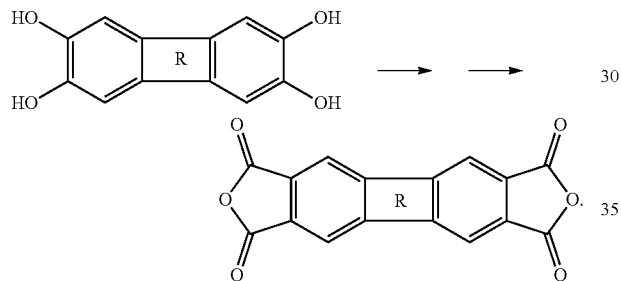

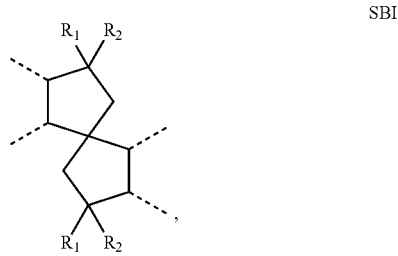

In a particular embodiment, the reaction scheme is as follows:

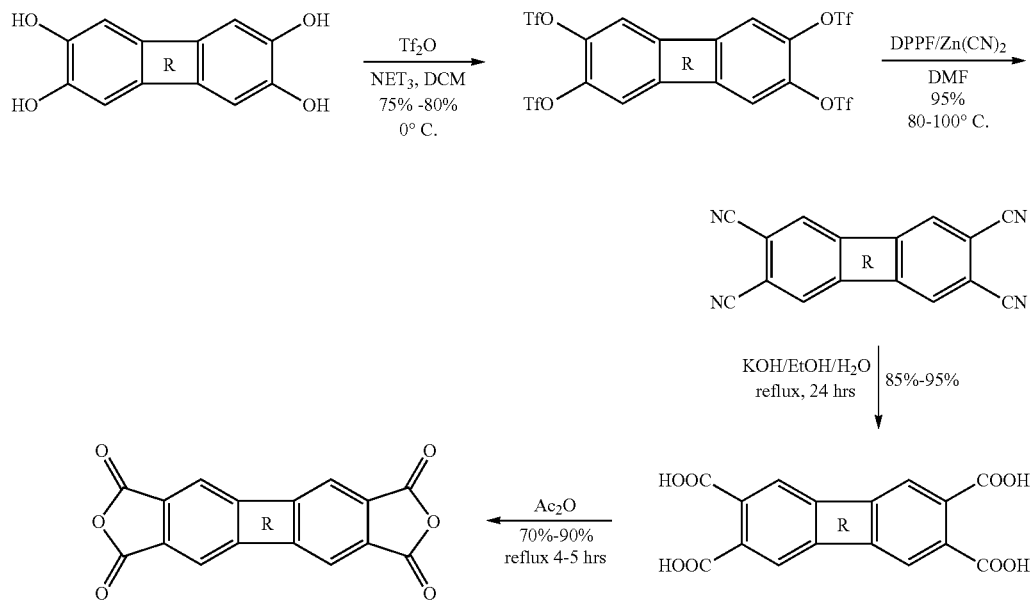

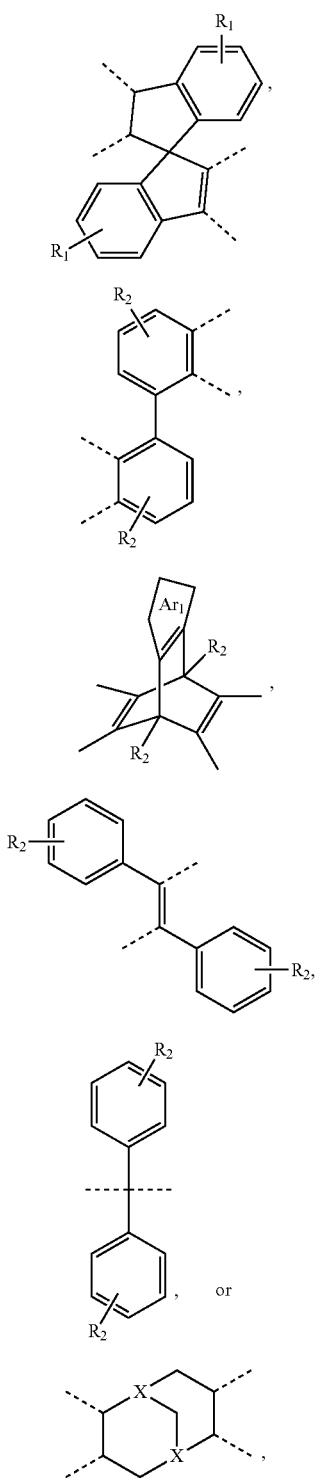

X = N, or H (spirobisindane (SBI)-, spirobifluorene (SBF)-, ethanoanthracene (EA (unmarked structure))-, binaphenyl (BIN)-, tetraphenylmethane (TPM)-, tetraphenylethane (TPE)-, troger's based (TB)- and its analogues). Each $R_1$ and $R_2$ is independently selected from: H or a linear or branched, substituted or unsubstituted, alkyl group. When the bond is directed to the middle of a ring (e.g., $R_1$ in each of the rings of SBF or each $R_2$ in each ring of each of BIN, TPE, and TPM), this indicates that 1 to 4 of the R groups are optionally attached to the ring and each R group is independently selected from other R groups attached to a ring. In an embodiment, each $R_1$ and $R_2$ can be independently selected from a methyl group, an ethyl group, a propyl group, and a butyl group (linear or branched), each substituted or unsubstituted. The phrase "independently selected from" can mean selection from $R_1$ and $R_2$ independent of one another, or can mean that in each instance of $R_1$ (as well as $R_2$) each $R_1$ is selected independently of the other $R_1$s (e.g., one $R_1$ can be a methyl group and the other $R_1$ can be a propyl group).

In an embodiment, $Ar_1$ can be an aryl group (e.g., phenyl) or a heteroaryl group (e.g., thiophene), where each is substituted or unsubstituted. In an embodiment, $Ar_1$ is selected from:

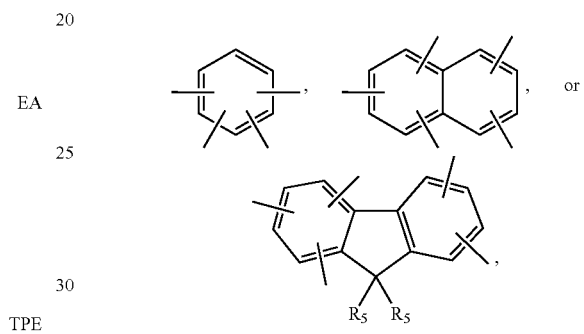

substituted or unsubstituted. Each $R_5$ can independently be H or a linear or branched, substituted or unsubstituted, alkyl group (e.g., methyl group). In an embodiment, $Ar_1$ can be selected from

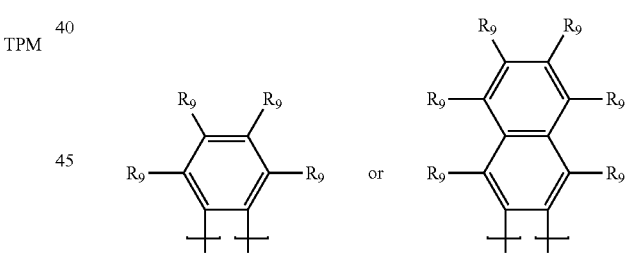

In an embodiment, each $R_9$ can be independently a linear or branched, substituted or unsubstituted, alkyl group (e.g., methyl group). Each $R_9$ can be independently selected of the other.

An embodiment of the present disclosure includes methods of making a multi-anhydride:

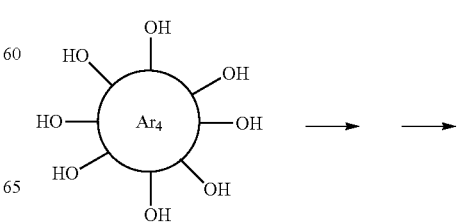

-continued

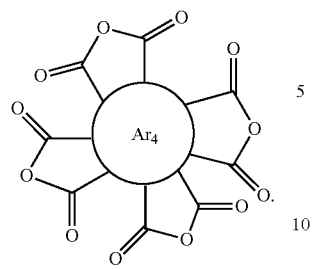

A particular embodiment includes:

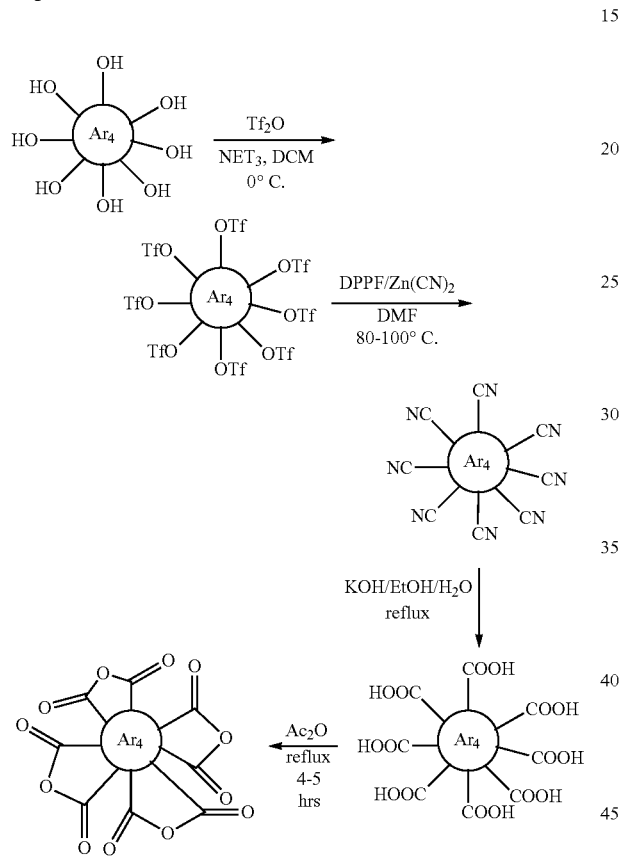

The reaction conditions (e.g., reactants, solvents, temp, pH, concentration, and the like) for each step of the reaction scheme can be adjusted consistent with the teachings of this disclosure as long as the final product is formed. For example, in step one the $NET_3$ can be changed to another base, DCM can be switched to another solvent such as chloroform, tetrahydrofuran, dimethylformamide and dimethylacetamide, and the like, while the temperature can about room temperature to the boiling point of the solvent. In step 2 the catalyst can be another palladium catalyst such as $PdCl_2$, $Pd_2(dba)_3$, $Pd(Ac)_2$, and the like, while the ligand can be a ligand selected from $PPh_3$, dba, dppe, dppp, and the like. The solvent can be changed from DMF to DMAc, NMP, and the like, while the temperature of the reaction can be about 40 to 150° C. In step 3 ratio of EtOH and $H_2O$ can be about 1:10 ratio to 10/1 ratio. In step 4 the reaction temperature can be about 100° C. to 140° C. and can reflux for about 1-48 hours, In an embodiment, $Ar_4$ can include the following structures:

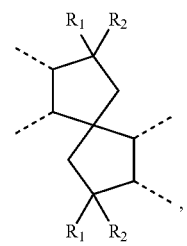

SBI

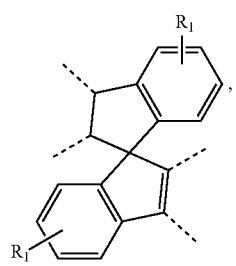

SBF

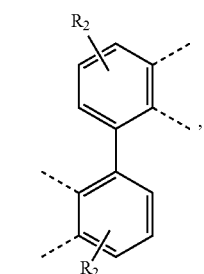

BIN

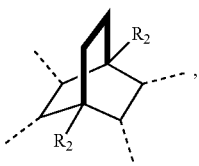

EA

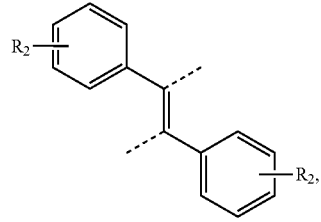

TPE

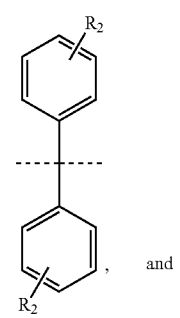

TPM and

-continued

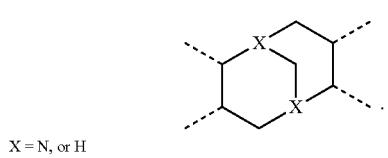

X = N, or H $R_1$ and $R_2$ are defined above.

An embodiment of the present disclosure includes a composition including a polyimide having the following structure:

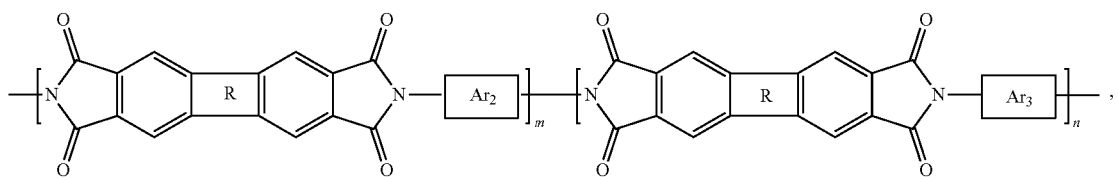

where $Ar_2$ and $Ar_3$ are aromatic diamines that are different from each other. In an embodiment, $Ar_2$ and $Ar_3$ can each independently be an aryl group or heteroaryl group.

In an embodiment, $Ar_2$ and $Ar_3$ can be an aryl group or heteroaryl group that can be derived from the following aromatic diamines: an aryl diamine group or a heteroaryl diamine group. In an embodiment, $Ar_2$ and $Ar_3$ can be:

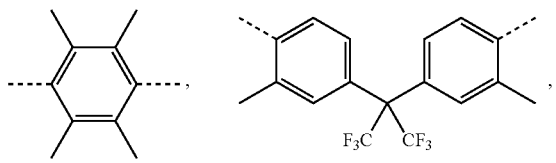

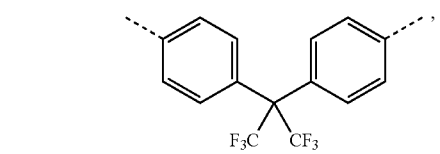

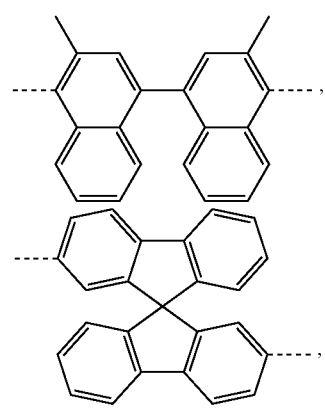

-continued

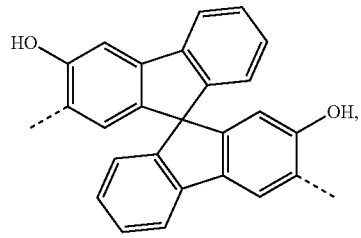

-continued

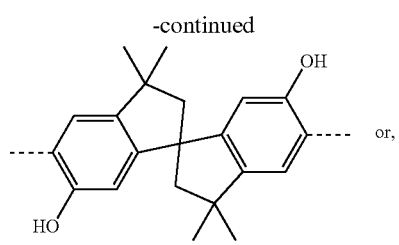

In an embodiment, $Ar_3$ can be derived from a heteroaryl diamine group and $Ar_3$ can be

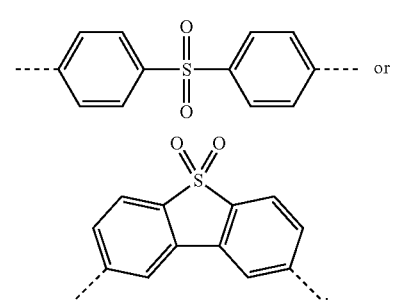

In an embodiment, $Ar_2$ and $Ar_3$ are different or can be the same. The subscript m and n can be independently 0 to 10000 or 1 to 10000. In an embodiment, R can include R as it is defined above.

An embodiment of the present disclosure includes a method of making a network polyimide, comprising:

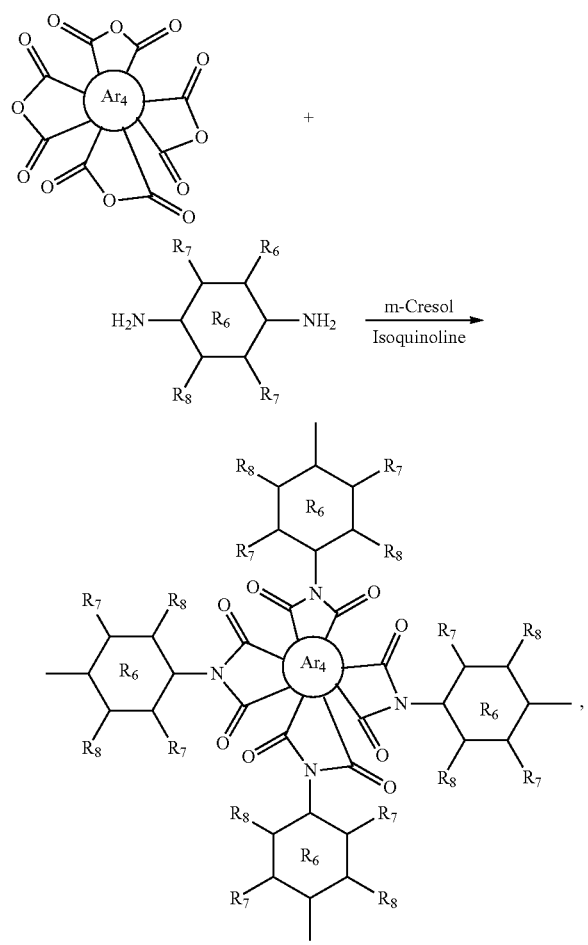

where Ar₄ is selected from the following structures:

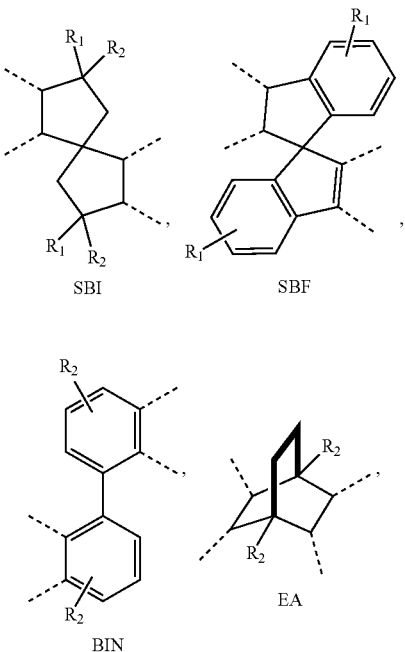

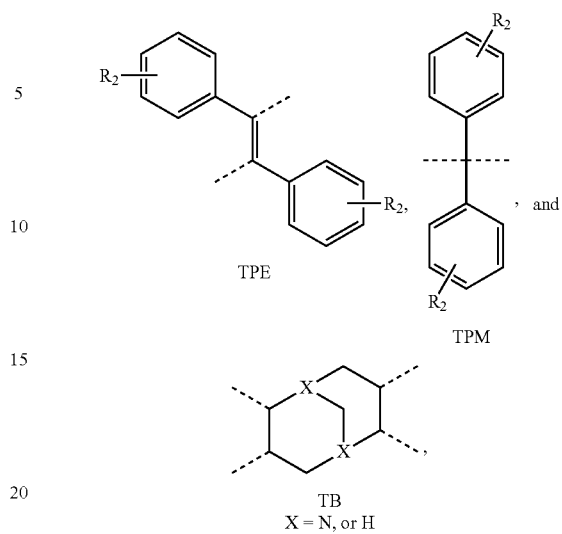

as well as analogues of each. In an embodiment, $R_8$ can be H, a substituted or unsubstituted aromatic group or a linear or branched, substituted or unsubstituted, alkyl group. In an embodiment, $R_7$ and $R_3$ are each independently H, a substituted or unsubstituted aromatic group or a linear or branched, substituted or unsubstituted, alkyl group, a hydroxyl group, a sulfonic group, and a thiol group. In an embodiment, the multi-amine can be a diamine, triamine, tetramine, or an amine having 5 or more amino groups.

The following are exemplary compounds that can be produced:

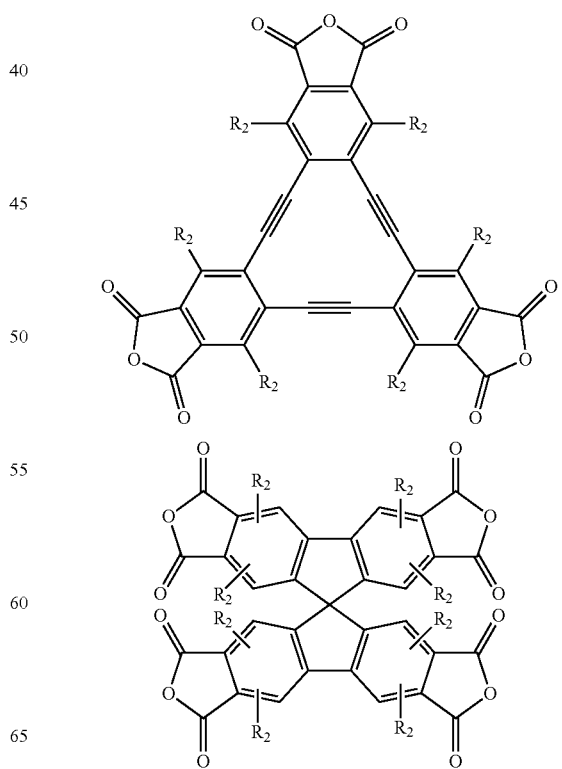

-continued

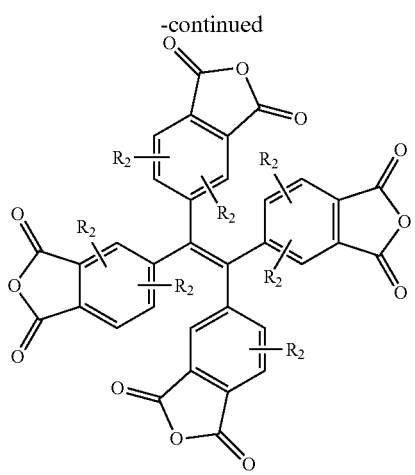

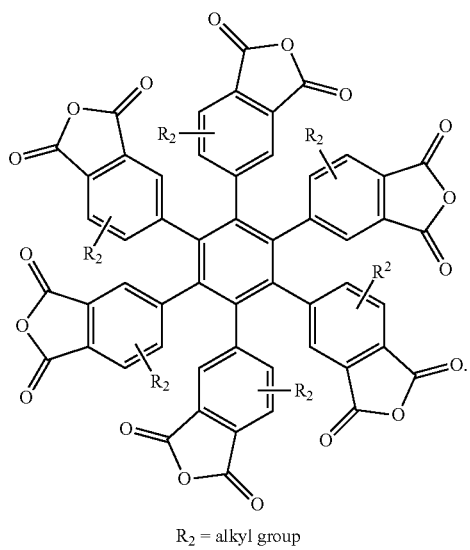

Y = C, Adamantane

R₂ = alkyl group

In general, the aromatic dianhydride is reacted with a multiamine in a solvent (e.g., NMP, DMAc, m-cresol or DMSO under certain conditions via one step heating method or two step method reaction) to form the aromatic dianhydride-based polyimide. The reaction conditions (e.g., reactants, solvents, temp, pH, concentration, and the like) for each step of the reaction scheme can be adjusted consistent with the teachings of this disclosure as long as the final product is formed.

EXAMPLES

Example 1

Synthesis of the Spirobisindane-Based Non-Extended Dianhydride

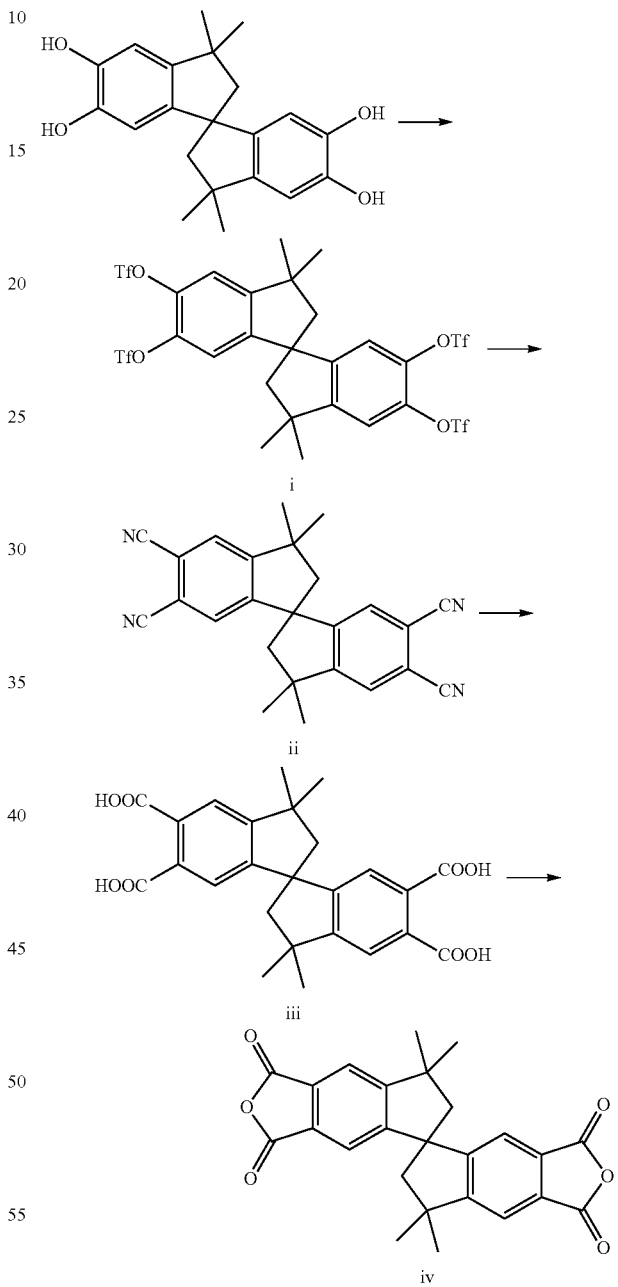

Synthesis of 3,3'3',3'-tetramethylspirobisindane-5,5',6,6'-tetratriflate. (i) To the solvent of 3,3'3',3',-tetramethylspirobisindane-5,5',6,6'-tetraol (334 mg, 1.00 mmol) in dichloromethane (10.0 mL) and triethyl amine (1.33 mL, 11 mmol), trifluoromethylsulfonic anhydride (1.86 mL, 11 mmol) was added dropwise over half an hour under ice-bath. The solution was stirred at room temperature for 4 hours before been poured to ice-water (30 mL). The organic phase was separated using a separation funnel and washed several times with diluted HCl (2N), and thereafter, dried with anhydrous magnesium sulfate. The solvent was removed by rota-evaporation and the residual was loaded to a column, an off-white powder (477 mg, yield: 55%) was obtained after column chromatography. TLC: Dichloromethane/petrol oil ether=1/4, $R_f$=0.6; $^1$H NMR (400 MHz, CDCl$_3$): δ 7.30 (s, 2H), 6.85 (s, 2H), 2.55 (d, 2H, J=12.9 Hz), 2.30 (d, 2H, J=13.4 Hz), 1.50 (s, 6H), 1.45 (s, 6H). $^{13}$C NMR (100 MHz, CDCl$_3$): δ 154.0, 149.9, 140.3, 139.9, 120.2, 120.1, 119.0, 117.7, 117.0, 116.9, 58.7, 57.7, 44.2, 31.3, 29.7.

Synthesis of 3,3'3',3'-tetramethylspirobisindane-5,5',6,6'-tetracyano. (ii) 3,3',3'' tetramethylspirobisindane-5,5',6,6'-tetratriflate (868 mg, 1.00 mmol), Pd$_2$(dba)$_3$ (42 mg), DPPF (55 mg) and ZnCN$_2$ (234 mg) was added to DMF (10 mL). After degas and refill with Ar for 3 times, the reaction system was gradually heated to 75° C. and kept for another half an hour, the color of the solution changed to light yellow. Another portion of ZnCN$_2$ (234 mg) was added and thereafter, the resulting system was heated overnight and then poured into water, filtrate and the solid was loaded to a column, the pure product can be obtained as an off-white powder (150 mg, yield: 40%) by column separation. TLC: dichloromethane, $R_f$=0.3; $^1$H NMR (400 MHz, CDCl$_3$): δ 7.65 (s, 2H), 7.16 (s, 2H), 2.52 (d, 2H, J=13.5 Hz), 2.28 (d, 2H, J=13.5 Hz), 1.48 (s, 6H), 1.40 (s, 6H). $^{13}$C NMR (100 MHz, CDCl$_3$): δ 158.3, 154.1, 129.5, 128.3, 115.9, 115.6, 115.4, 115.2, 58.2, 44.8, 31.2, 29.4.

Synthesis of the 3,3',3',3'-tetramethyispirobisindane-5,5',6,6'-tetracarboxlic acid. (ii) 3,3'3',3',-tetramethylspirobisindane-5,5',6,6'-tetracyano (3.76 g, 10.0 mmol) was dispersed in ethanol (60 mL). To it, KOH (11.6 g, 200 mmol) dissolved in water (60 mL) was added dropwise. The reaction system was thereafter heated to reflux for 12 hrs. a clean solution was formed and cooled to room temperature, the solution was poured into cold HCl (6N, 200 mL), stirred at room temperature for 2 hrs. Remove most of the ethanol and the precipitate was filtrate and washed with diluted HCl (2N) for 3 times. An off-white solid (4.00 g, yield: 88.1%) was obtained after drying in the 70° C. oven for 12 hrs. $^1$H NMR (400 MHz, DMSO-d$_6$): δ 13.1 (s, 4H), 7.56 (s, 2H), 7.02 (s, 2H), 2.41 (d, 2H, J=13.1 Hz), 2.23 (d, 2H, J=13.1 Hz), 1.40 (s, 6H), 1.35 (s, 6H), Synthesis of the 3,3'3',3'-tetramethyispirobisindane-5,5',6,6'-tetracarboxlic anhydride. (iv) The 3,3'3',3',-tetramethylspirobisindane-5,5',6,6'-tetracarboxlic acid (1.00 g, 2.2 mmol) was added to acetic anhydride (1.00 mL). The system was heated up to 120° C. and kept for 4 hrs. An off-white precipitate was formed. The solid was thereafter collected by filtration and washed 3 times with cold acetic anhydride. The white powder was dried in vacuum oven at 120° C. till a constant weight. The powder (700 mg, yield: 69.2%) can be used directly for polymerization reactions, $^1$H NMR (400 MHz, CDCl$_3$): δ 7.70 (s, 2H), 7.20 (s, 2H), 2.54 (d, 2H, J=13.5 Hz), 2.30 (d, 2H, J=13.5 Hz), 1.49 (s, 6H), 1.41 (s, 6H). Anal. Calcd for. C, 72.11; H, 4.84; Found: 71.90; H, 4.80%.

Example 2

Synthesis of Ethanoanthracene-Based Non-Extended Dianhydride

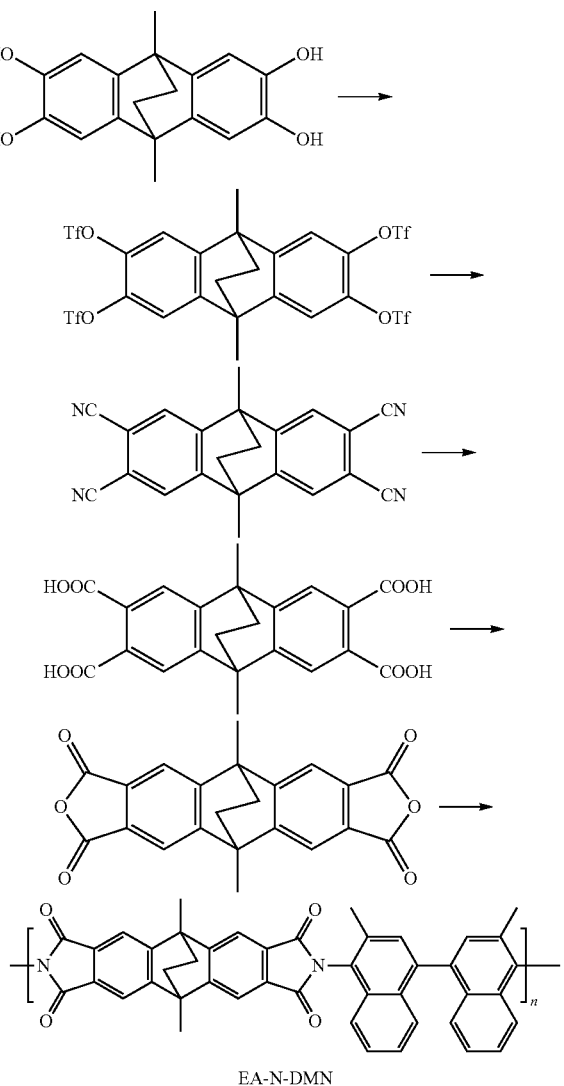

EA-N-DMN

Scheme S2. Design and synthesis of the ethanoanthracene-based dianhydride and microporous polyimides Synthesis of 9,10-dimethyl-ethanoanthracene-2,3,6,7-tetra-triflate. 9,10-dimethyl-ethanoanthracene-2,3,6,7-tetraol (9.00 g, 30.2 mmol) was added to the mixed solvent of dichloromethane (260 mL) and triethyl amine (40.0 mL, 337 mmol). The system was cooled in ice-bath for half an hour. To it, trifluoromethylsulfonic anhydride (59.0 mL, 349 mmol) was added dropwise over half an hour. The solution was stirred at room temperature for 4 hours before been poured to ice-water (300 mL). The organic phase was separated using a separation funnel and washed several times with diluted HCl (2N), and thereafter, dried with anhydrous magnesium sulfate. The solvent was removed by rota-evaporation and the residual was loaded to a column, an off-white powder (13.0 g, yield: 52.1%) was obtained after column chromatography. TLC: Dichloromethane/petrol oil ether=1/2, $R_f$=0.6; $^1$H NMR (400 MHz, CDCl$_3$): δ 7.40 (s, 4H), 2.03 (s, 6H), 1.77 (s, 4H).

Synthesis of enthanoanthrance-2,3,6,7-tetracyano. 9,10-dimethyl-ethanoanthracene-2,3,6,7-tetra-trifluoromethyl-sulfonate (14.5 g, 17.6 mmol), Zn(CN)$_2$ (1.50 g, 12.8 mmol), Pd$_2$(dba)$_3$ (800 mg, 0.76 mmol) and DPPF (1.60 g, 2.89 mmol) was added to anhydrous DMF (80 mL), which was degassed by a vacuum pump and refilled with N$_2$ for three times, The solution was thereafter heated to 100° C. and kept for another half an hour. Three portions of Zn(CN)$_2$ (1.50 g, 1.50 g, 1.50 g) was added to the reaction system in another one hour. After that, the solution was kept at 100° C. for 1 hour, and then poured into methanol (200 mL). A large quantity of yellow solid was formed, filtrated and loaded to a column, an off-white product (5.10 g, yield: 86.8%) was obtained after column separation. TLC: dichloromethane, $R_f$=0.3; $^1$H NMR (400 MHz, DMSO-d$_6$): δ 8.15 (s, 4H), 2.05 (s, 6H), 1.66 (s, 4H).

Synthesis of 9,10-dimethylethanoanthrance-2,3,6,7-tetracarboxylic acid. The tetracyano intermediate (v) (1.78 g, 5.33 mmol) was dispersed in ethanol (30 mL). To it, KOH (6.18 g, 107 mmol) dissolved in water (30 mL) was added dropwise. The reaction system was thereafter heated to reflux for 12 hrs, a clean solution was formed and cooled to room temperature, the solution was poured into cold HCl (6N, 100 mL), stirred at room temperature for 2 hrs. Remove most of the ethanol and the precipitate was filtrate and washed with diluted HCl (2N) for 3 times. An off-white solid (1.30 g, yield: 62.8%) was obtained after drying in the 70° C. oven for 12 hrs. $^1$H NMR (400 MHz, DMSO-d$_6$): δ 13.1 (s, 4H), 7.61 (5, 4H), 2.01 (s, 6H), 1.65 (s, 4H).

Synthesis of 9,10-dimethylethanoanthrance-2,3,6,7-tetracarboxylic anhydride 9,10-dimethylethanoanthrance-2,3,6,7-tetracarboxylic acid (400 mg, 0.97 mmol) was added to acetic anhydride (1.00 mL). The system was heated up to 120° C. and kept for 4 hrs. An off-white precipitate was formed. The solid was thereafter collected by filtration and washed 3 times with cold acetic anhydride. The white powder was dried in vacuum oven at 120° C. till a constant weight. The powder (300 mg, yield: 80.2%) can be used directly for polymerization reactions. $^1$H NMR (500 MHz, CDCl$_3$): δ 7.97 (s, 4H), 2.19 (s, 6H), 1.80 (s, 4H).$^{13}$C NMR (125 MHz, CDCl$_3$): 162.8, 153.7, 129.9, 118.3, 44.3, 34.3, 18.5; HRMS for [C$_{22}$H$_{15}$O$_6$]$^+$: Calcd for: 375.0863; Found: 375.0863; Anal. Calcd for. C, 70.59; H, 3.77. Found: C, 70.20; H, 3.56.

Synthesis of EA-N-DMN. EA-N-DA (196.6 mg, 0.526 mmol) and 3,3-Dimethylnaphthidine (164.2 mg, 0.526 mmol) were added to m-cresol (1.9 mL). The system was heated to 60° C. and kept for 1 hr to form a viscosy solution. 1 drop of isoquinoline was added and the solution was thereafter heated to 180° C. and kept for 3 hrs. Finally, a highly viscosity solution was formed and precipitated to methanol (100 mL). The remaining m-cresol was removed by Soxhlet extractor using methanol. The polymer was re-dissolved in chloroform and precipitated in methanol twice. An off-white powder (340 mg, yield: 94.5%) was obtained after drying in vacuum oven for 24 hrs at 120° C. $^1$H NMR (500 MHz, CDCl$_3$): δ 8.10 (s, 4H), 7.26-7.65 (m, 10H), 2.30-2.45 (m, 12H), 2.04 (s, 4H). FT-IR (polymer film, v, cm$^{-1}$): 3055 (m, str C—H), 1780, 1714 (s, str, imide), 1600, 1452 (m, str, Ph), 1311, 1286 (s, str, C—N), 747 (s, astr, imide); Anal. Calcd. for: C, 80.96; H, 4.94; N, 4.29. Found: C, 78.08; H, 4.60; N, 3.80; Molecular weight (GPC in chloroform) M$_n$=13×10$^4$; PDI=2.1. T$_d$=300° C.; S$_{BET}$=720 m$^2$/g. (Lit. 600 m$^2$/g)

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, "about 0" can refer to 0, 0.001, 0.01, or 0.1. In an embodiment, the term "about" can include traditional rounding according to significant figures of the numerical value. In addition, the phrase "about 'x' to 'y'" includes "about 'x' to about 'y'":

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

I claim:

1. A method of making a dianhydride comprising:

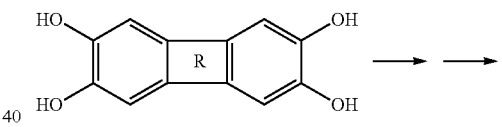

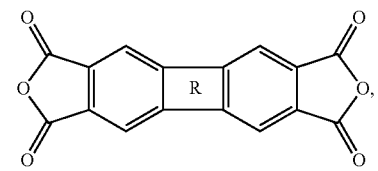

wherein R is selected from the following structures:

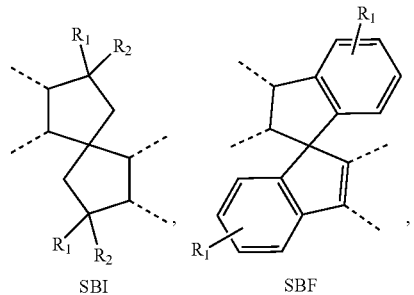

27

-continued

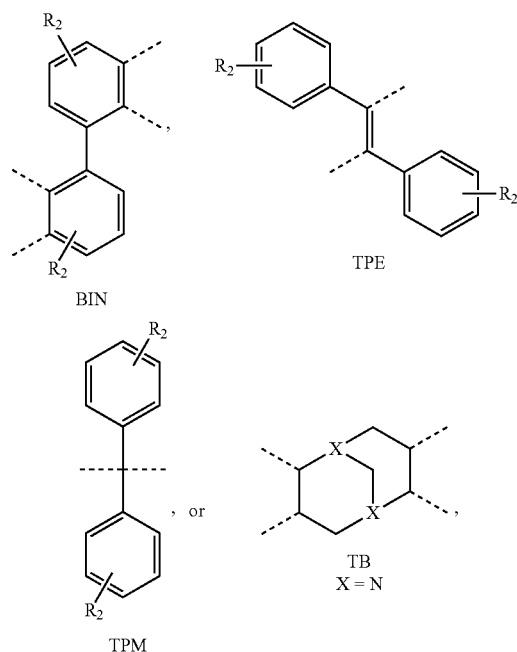

BIN

TPE

TPM

TB
X = N wherein each $R_1$ and $R_2$ are independently selected from the group consisting of: H, a linear or branched, substituted or unsubstituted, alkyl group, wherein when the bond is directed to the middle of a ring, this indicated that 1 to 4 of the R groups is optionally attached to the ring and each R group is independently selected from other R groups attached to a ring, and wherein the dashed lines indicate the R group is bonded directly to the aromatic group of each phthalic anhydride moiety of the dianhydride product.

2. A method of making a dianhydride comprising:

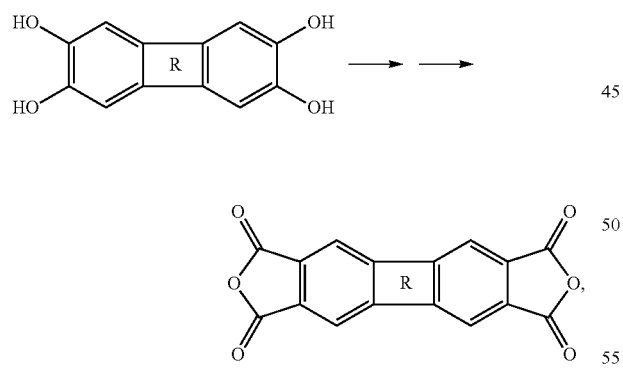

28 wherein R is selected from the following structures:

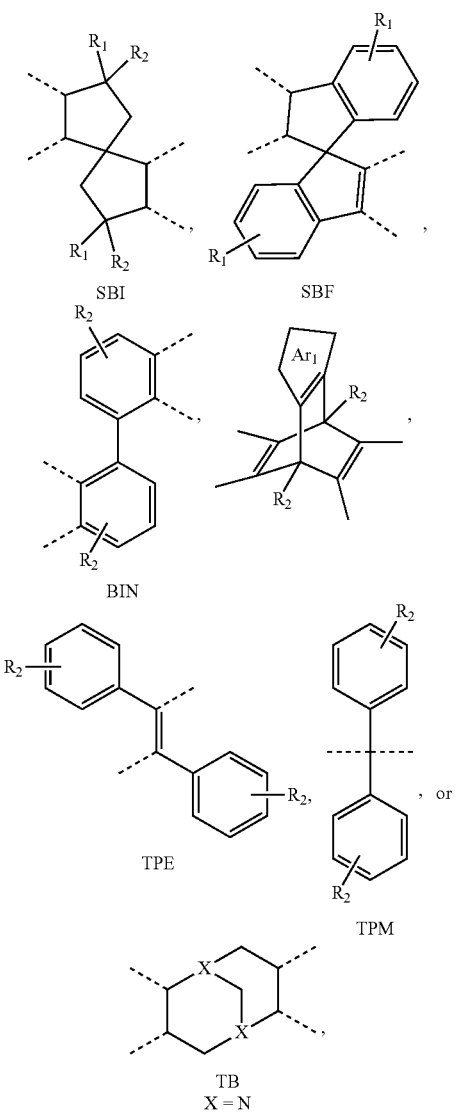

SBI

SBF

BIN

TPE

TPM

TB
X = N wherein each $R_1$ and $R_2$ are independently selected from the group consisting of: H, a linear or branched, substituted or unsubstituted, alkyl group, wherein when the bond is directed to the middle of a ring, this indicated that 1 to 4 of the R groups is optionally attached to the ring and each R group is independently selected from other R groups attached to a ring, wherein $Ar_1$ is selected from the group consisting of: an aryl group and a heteroaryl group where each are substituted or unsubstituted, wherein the method comprises:

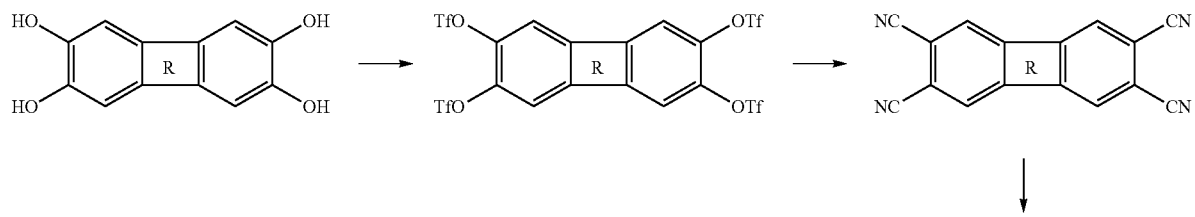

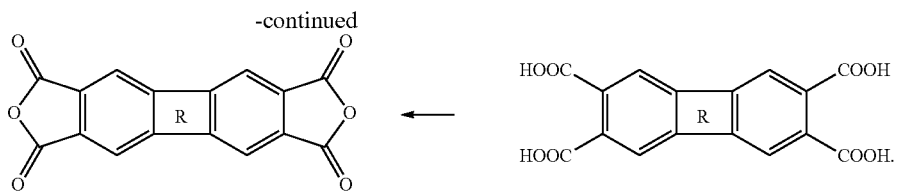
3. The method of claim 1, wherein R is:
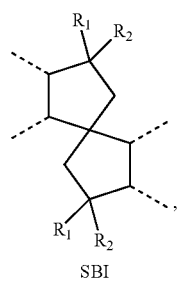
wherein $R_1$ and $R_2$ are methyl groups, whereby the dianhydride has the following structure:
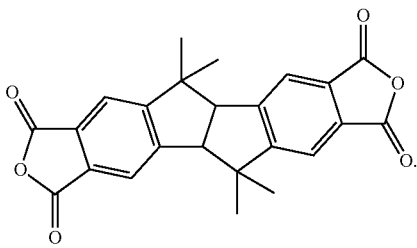 [SMILES: CC1(C)c2cc3c(cc2C2C1c1cc4c(cc1C2(C)C)C(=O)OC4=O)C(=O)OC3=O]
4. The method of claim 1, wherein the method comprises:
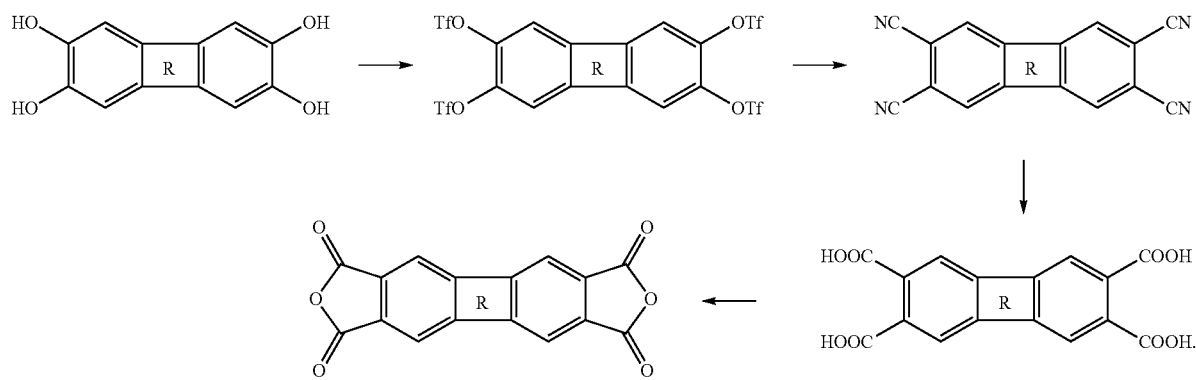
5. The method of claim 2, wherein R is:
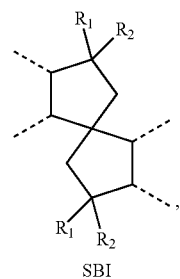
wherein $R_1$ and $R_2$ are methyl groups.
* * * * *